United States Patent [19]

Takamatsu, deceased et al.

[11] Patent Number: 4,475,541

[45] Date of Patent: Oct. 9, 1984

[54] ENDOSCOPE APPARATUS

[75] Inventors: Takeshi Takamatsu, deceased, late of Hachioji, Japan; by Tokuyuki Takamatsu, legal representative, Tokyo, Japan

[73] Assignee: Olympus Optical Co., Ltd., Tokyo, Japan

[21] Appl. No.: 437,443

[22] Filed: Oct. 28, 1982

[30] Foreign Application Priority Data

Nov. 4, 1981 [JP] Japan .................. 56-176915

[51] Int. Cl.³ .............................................. A61B 1/06
[52] U.S. Cl. .................................... 128/6; 354/62
[58] Field of Search ........................ 128/4–8; 354/62; 358/98, 141, 142; 362/32

[56] References Cited

U.S. PATENT DOCUMENTS

| | | |
|---|---|---|
| 4,281,910 | 8/1981 | Takayama .................. 128/4 |
| 4,349,014 | 9/1982 | Takamatsu .................. 128/6 |
| 4,403,605 | 9/1983 | Tamikawa .................. 128/6 |

FOREIGN PATENT DOCUMENTS

| | | | |
|---|---|---|---|
| 17464 | 10/1980 | European Pat. Off. ....... | 128/6 |
| 25958 | 4/1981 | European Pat. Off. ....... | 128/6 |

*Primary Examiner*—Edward M. Coven
*Assistant Examiner*—Max F. Hindenburg

[57] ABSTRACT

An endoscope apparatus comprises a light source unit including a controlling station transmission circuit to serve as a controlling station, and an endoscope unit and an endoscopic camera unit individually including controlled station transmission circuits to serve as controlled stations. The controlling station transmission circuit checks unregistered addresses on its own address table a fixed number of times every time an operation sequence is completed. If a unit connected to the light source unit is an unregistered unit, the address of the unregistered unit is registered on one of the unregistered addresses on the address table.

4 Claims, 6 Drawing Figures

ENDOSCOPE APPARATUS

BACKGROUND OF THE INVENTION

This invention relates to an endoscope apparatus, and more specifically, to an endoscope apparatus capable of data transmission among an endoscope unit, a light source unit, and an optional unit.

An endoscope apparatus in which data are transmitted among an endoscope unit, a light source unit, and a camera unit to control several operations, such as air feed, water feed, suction, photographing, etc. has been conventionally developed. In this endoscope apparatus, the light source unit functions as a controlling station, while the endoscope unit and the camera unit serve as controlled stations. According to the conventional endoscope apparatus, it is a long time before the light source unit starts an address check for the control of a unit to be controlled. If the camera unit is attached to the eyepiece section of the endoscope unit while the light source unit is controlling only the endoscope unit, it takes a long time for the light source unit to perform an address check for the camera unit and recognize the connection of the camera unit before transmitting initial data to the camera unit. Thus, if an operator operates the camera unit before the initial data is transmitted thereto, the camera unit may suffer erroneous operation.

SUMMARY OF THE INVENTION

Accordingly, the object of this invention is to provide an endoscope apparatus free from erroneous operation at the attachment or removal of an endoscope unit, light source unit, and camera unit.

According to this invention, there is provided an endoscope apparatus in which a controlling station in one unit, including a light source unit, an endoscope unit, and an optional unit, has means for checking the connection of a fixed number of unregistered units with every completion of an operation sequence, and the unregistered units have means for responding to the check of the checking means.

BRIEF DESCRIPTION OF THE DRAWINGS

FIG. 6 is an operating flow chart of a transmission circuit in a camera unit.

DETAILED DESCRIPTION OF THE PREFERRED EMBODIMENT

Figure 1:
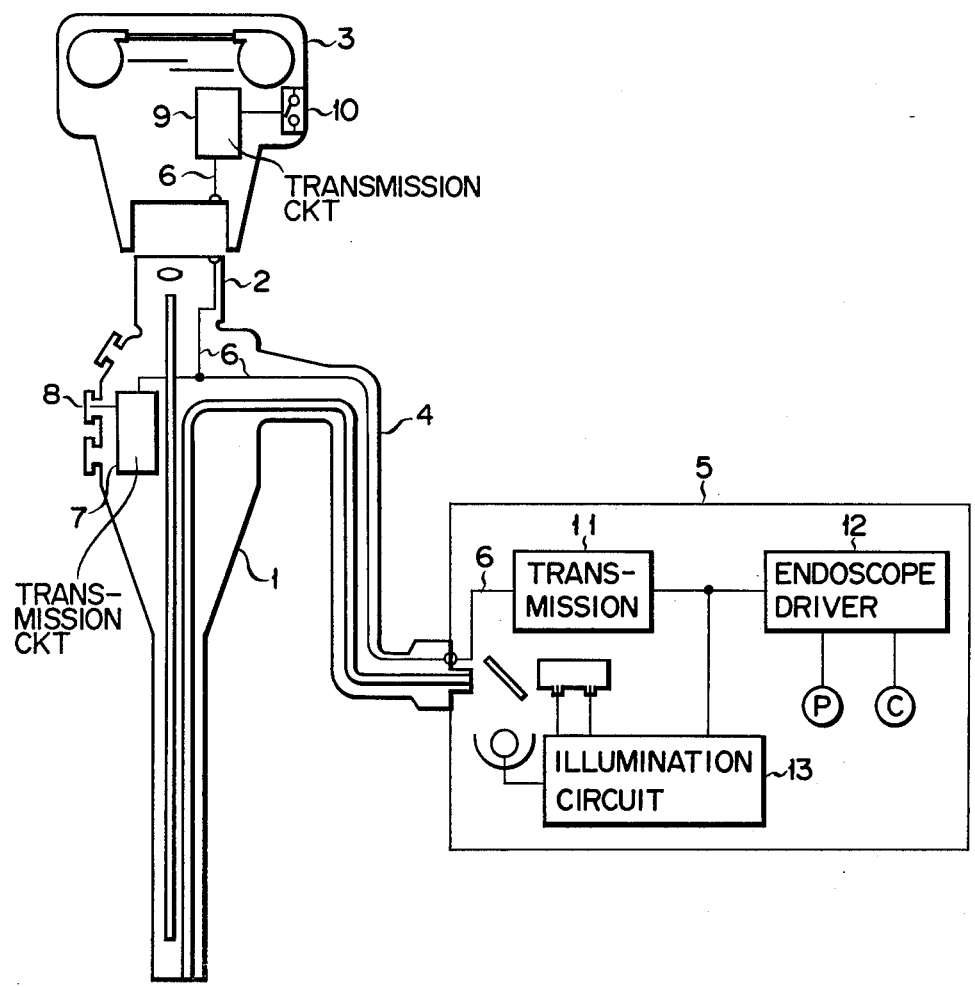
FIG. 1 is a schematic circuit diagram of an endoscope apparatus according to one embodiment of this invention.

Referring now to FIG. 1, a camera unit 3 as one of various units can be attached to an eyepiece section 2 of an endoscope unit 1, and a connector section 4 of the endoscope unit 1 is connected to a light source unit 5. A transmission circuit 7 of the endoscope unit 1 is connected to operating switches, including an air feed switch 8, and is also connected to a transmission circuit 9 of the camera unit 3 and a transmission circuit 11 of the light source unit 5 by means of a transmission line 6.

The transmission circuit 11 of the light source unit 5 functions as a controlling station, while the transmission circuits 7 and 9 of the endoscope unit 1 and the camera unit 3 are controlled stations. The transmission circuit 9 is connected with operating switches, such as a release switch 10, of the camera unit 3, and the transmission circuit 11 is connected to an endoscope driver circuit 12 for controlling air feed, water feed and suction, and to an illumination control circuit 13 for illumination control for photographing.

Figure 2:
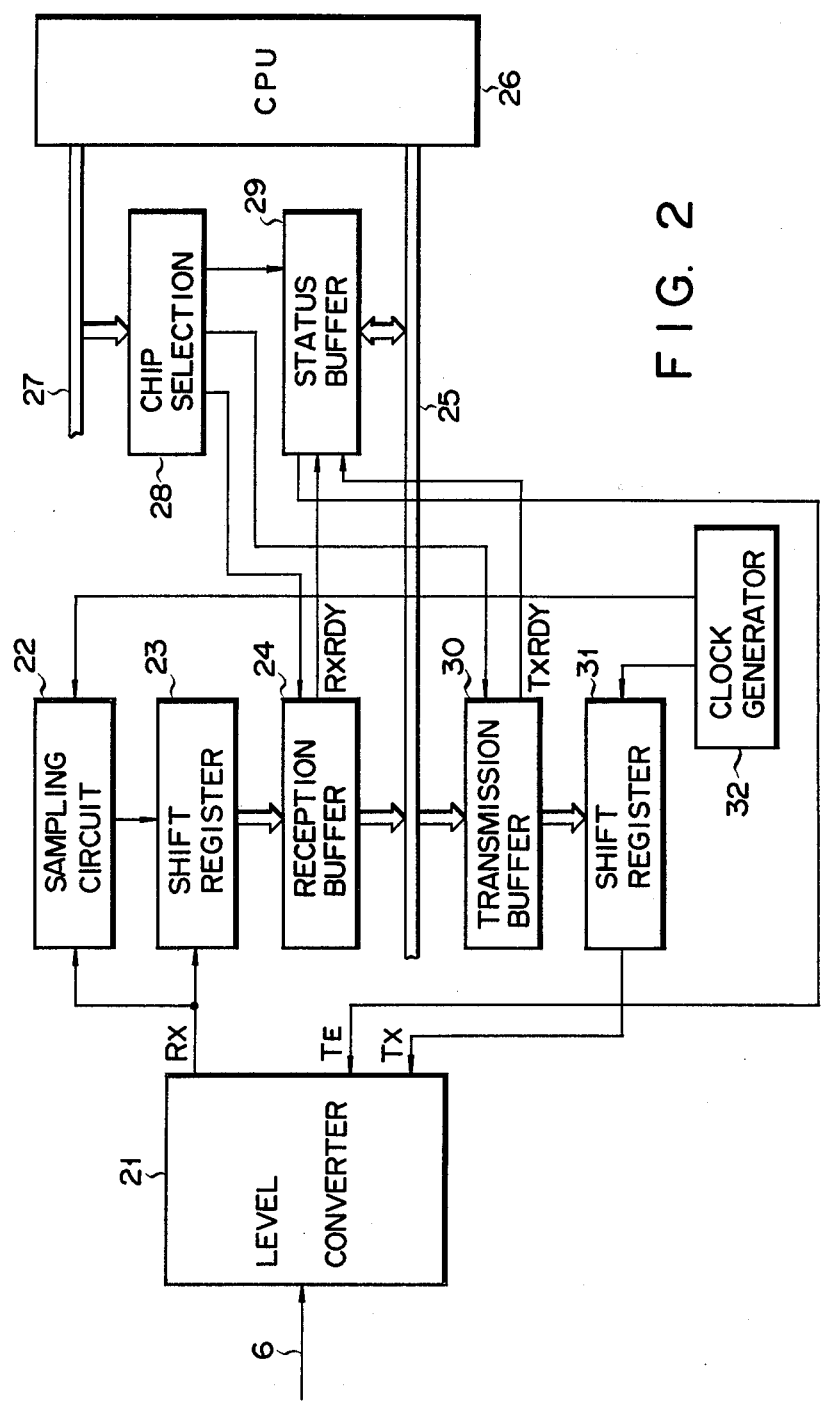
FIG. 2 is a circuit diagram of a transmission circuit shown in FIG. 1.

FIG. 2 shows a circuit configuration of the transmission circuits 7, 9 and 11. In this circuit arrangement, a level converter 21 is connected to the transmission line 6. An output terminal Rx of the level converter 21 is connected to a sampling circuit 22 and a shift register 23. The shift register 23 is also connected with the output terminal of the sampling circuit 22. The output port of the shift register 23 is connected to a data bus 25 through a reception buffer 24. The data bus 25 is connected to a CPU 26. An address bus 27 connected to the CPU 26 is also connected to a chip selector 28. The output terminal of the chip selector 28 is connected to the reception buffer 24, a status buffer 29, and a transmission buffer 30. The input-output port and the signal output terminal of the status buffer 29 are connected to the data bus 25 and the level converter 21, respectively. The status buffer 29 is connected to the reception and transmission buffers 24 and 30 from which it receives signals RxRDY and TxRDY, respectively. The signal RxRDY indicates the reception of reception data for one character, while the signal TxRDY indicates that the transmission buffer 30 is ready for the reception of transmission data. The output port of the transmission buffer 30 is connected to a shift register 31. The output terminal of the shift register 31 is connected to an input terminal Tx of the level converter 21. A clock pulse generator 32 is connected to the sampling circuit 22 and the shift register 31.

Figure 3:
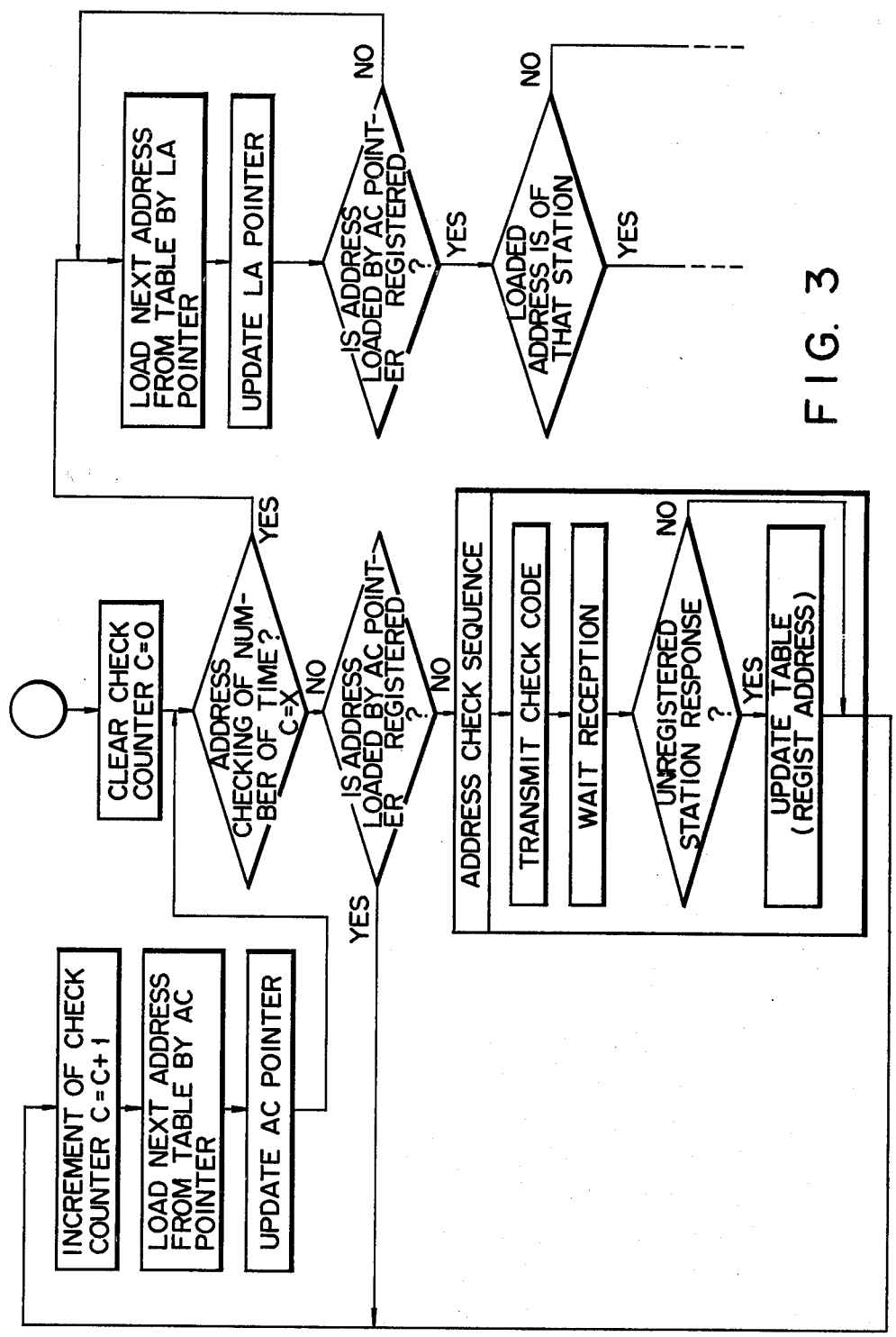
FIG. 3 is a flow chart illustrating the operation of the endoscope apparatus.
Figure 4:
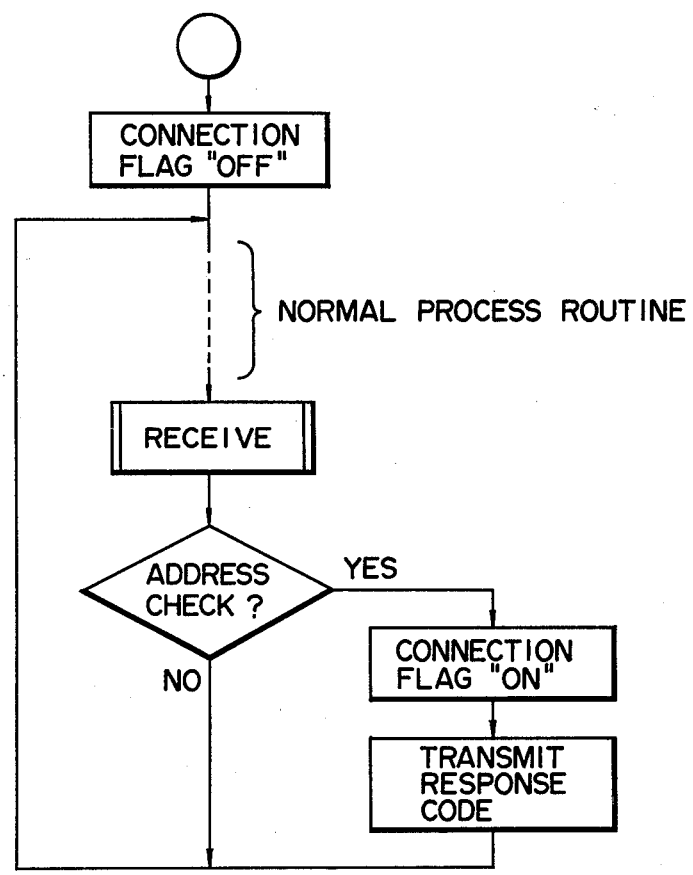
FIG. 4 shows a format of an address table.
Figure 5:
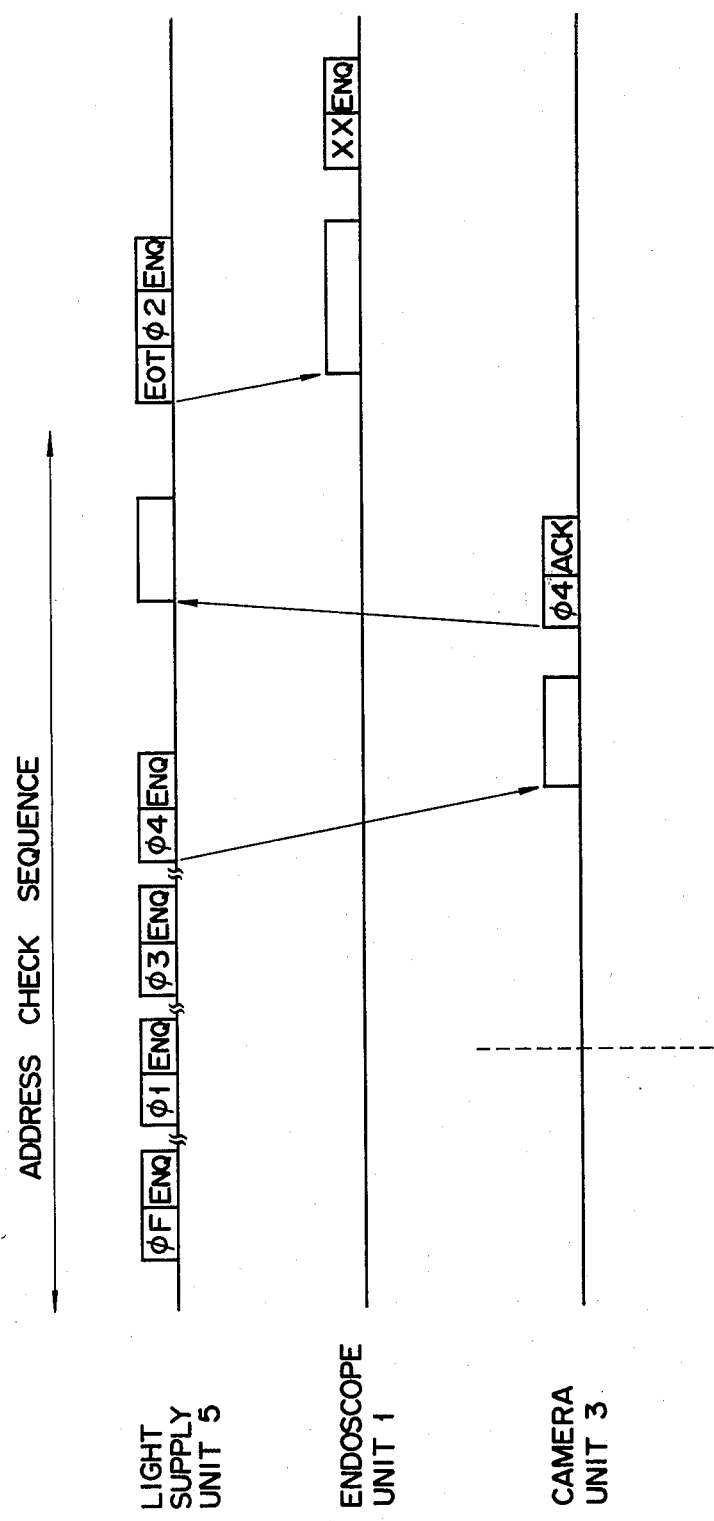
FIG. 5 is a time chart showing an address check sequence.

There will now be described the operation of the aforementioned endoscope apparatus. When the endoscope unit 1 and the light source unit 5 are connected to each other, the transmission circuit 11 of the light source unit 5 as the controlling station operates in accordance with the flow chart of FIG. 3. Namely, at the end of a controlling station sequence including polling and selection, a check counter C of the CPU 26 is cleared, and then address checking is repeated x number of times, e.g., four times. In this case, the transmission circuit 11 checks addresses on the address table of FIG. 4, and delivers a check signal to the transmission line 6. In FIG. 4, an AC pointer for selecting an unregistered address designates an address F, so that the transmission circuit 11 delivers a code F·ENQ to the transmission line 6, and waits for a response for a fixed time. If there is no response, the check counter C is incremented. The next address on the address table is loaded into the CPU 26 by the AC pointer. Thereafter, the AC pointer is updated. Then, a decision is made as to whether the address check has been repeated x number of times or not. If the decision is "no", it is decided whether the address loaded by the AC pointer is registered or not. At this time, the AC pointer designates a registered address "0", so that the decision proves to be "yes", and the AC pointer proceeds to the next address "1". Since the address "1" is unregistered, the decision on registration proves to be "no", and an address check sequence is entered. In this sequence, a check code 1·ENQ is transmitted, and a response is awaited. If there is no response, the AC pointer proceeds to an address "2". Since the address "2" is registered, the AC pointer proceeds further to an address "3". Thus, the address check is performed, and check codes 3·ENQ and 4·ENQ are transmitted. If the unregistered camera unit 3 is attached to the eyepiece section 2 of the endoscope unit 1 during the address check to cause a CPU in the transmission circuit 9 of the camera unit 3 to respond to the address code 4·ENQ and to deliver a response code 4·ACK, as shown in FIG. 5, then an address "4" on the address table is registered. Namely, an unregistered flag "0" of the address "4" is modified into a registered flag "8". As a result, the transmission circuit 11 of the light source unit 5 detects the connection of the camera unit 3. When the address check is thus repeated x number of times or four times, a registered address is selected among the addresses on the address table according to the designation by an LA pointer. If the LA pointer designates the address "0", that is, if the light source unit 5 is selected, then the CPU in the transmission circuit 11 as the controlling station executes a sequence starting from selection. In FIG. 4, the LA pointer designates the address "2", so that the CPU in the transmission circuit 11 executes polling. In the polling, when the CPU in the transmission circuit 11 as the controlling station receives a demand for air feed by the operation of the air feed switch 8 from the CPU in the transmission circuit 7 as the controlled station, it gives the endoscope driver circuit 12 an instruction for air feed. In response to the air feed instruction, the endoscope driver circuit 12 drives an air feed system, including an air feeding pump P and an air feeding valve, to feed the endoscope unit 1 with air. When the transmission circuit 9 of the camera unit 3 demands photographing by the operation of the release switch 10, the CPU in the transmission circuit 11 receives the demand and gives the illumination control circuit 13 an instruction for photographing. In response to the photographing instruction, the illumination control circuit 13 performs photographing operations including emission of photographing light and automatic exposure. The transmission circuit 9 of the camera unit 3 operates in accordance with the flow chart of FIG. 6. When a series of operations for information transmission is ended in this way, the transmission circuit 11 as the controlling station completes an operation sequence. At this time, the transmission circuit 11 repeats again the aforesaid address check x number of times.

According to this invention, as described above, every time a transmission circuit as a controlling station completes an operation sequence, an unregistered address of a transmission circuit as a controlled station is checked a fixed number of times. Accordingly, a connected unit can be identified quickly, and will never suffer incorrect operation even if it is operated immediately after connection.

According to the above embodiment, address checking is performed four times. This number of times is equal to the square root of the number of all the addresses, i.e., sixteen addresses. If address checking were performed only a few times, it would take a long time to complete the checking of all the addresses since a series of operation sequences are executed after each sequence of address checking. If address checking is performed a large number of times, it takes a long time to complete each sequence of address checking, and the interval between each execution of the series of operation sequences is long. It is therefore desirable that the number of the addresses checking times be close to the square root of the number of all the addresses.

In the above embodiment, the camera unit is used for the unregistered unit. This unit may, however, be replaced with any other unit that can be used with an endoscope apparatus, such as a superimposed data setting unit, television unit, ultrasonic diagnosis unit, laser unit, etc. The endoscope apparatus may be fitted with a plurality of optional units instead of a single optional unit. When the attached unit is removed, there is no response to the polling of the controlling station. Such "no response" can be recorded on the address table so that the removal of the unit may be noticed. If the removed unit is mounted again, therefore, it can be identified properly. In the above embodiment, the transmission circuit of the light source unit is used as a controlling station, and those of the other units are used as controlled stations. However, the controlling station transmission circuit may be provided in any unit. The polling-selection system for the transmission routine may be replaced with any other system, such as JISC6362 basic data transmission control routine. The check code for the address check is not limited to the address-ENQ form, and may be composed of only an address or any other character. Likewise, the response code may have any other form than the address-ACK form.

What is claimed is:

1. An endoscope apparatus which comprises an endoscope unit for the observation of the interior of a body cavity, a light source unit coupled to the endoscope unit to deliver illumination into the body cavity through a light guide of the endoscope unit, and at least one optional unit coupled to at least one of the endoscope unit and the light source unit, said apparatus further comprising:

a controlling transmission circuit as a controlling station in one of said endoscope unit, said light source unit, and said optional unit; and controlled transmission circuits as controlled stations in the other units, said controlling station transmission circuit including means for registering the address of said unit connected thereto, and checking means for checking a fixed number of unregistered addresses of said address registering means for transmitting connection check signals every time an operation routine is completed, each said controlled station transmission circuit including responding means for producing a response signal in response to said connection check signals, and said controlling station transmission circuit further including means for recognizing the response signal of said responding means and registering on said unregistered address the address of an unregistered unit having the responsive controlled station transmission circuit.

2. The endoscope apparatus according to claim 1, wherein said controlling station transmission circuit is provided in said light source unit.

3. The endoscope apparatus according to claim 2, wherein said optional unit is a camera unit.

4. The endoscope unit according to claim 1, wherein said fixed number of addresses checked by said checking means approximates the square root of the total number of addresses that can be registered by said address registering means.

* * * * *